United States Patent [19]
Runge

[11] Patent Number: 6,127,400
[45] Date of Patent: Oct. 3, 2000

[54] SALTS OF DIAMINE PYRROLIDINE

[75] Inventor: Thomas A. Runge, Scotts, Mich.

[73] Assignee: Pharmacia & Upjohn Company, Kalamazoo, Mich.

[21] Appl. No.: 09/320,939

[22] Filed: May 27, 1999

Related U.S. Application Data

[60] Provisional application No. 60/087,194, May 29, 1998, and provisional application No. 60/101,848, Sep. 25, 1998.

[51] Int. Cl.$^7$ ......................... A61K 31/40; A61K 31/402; A61P 31/04; A61P 31/40; C07D 207/09
[52] U.S. Cl. ............................................ 514/408; 548/566
[58] Field of Search .............................. 548/566; 514/408

[56] References Cited

U.S. PATENT DOCUMENTS

| | | | |
|---|---|---|---|
| 3,390,180 | 6/1968 | Fontana et al. | 260/582 |
| 3,436,420 | 4/1969 | Dudzunski | 260/583 |
| 3,927,102 | 12/1975 | Chiou et al. | 260/283 N |
| 5,130,490 | 7/1992 | Albright, Jr. | 564/438 |
| 5,416,222 | 5/1995 | Hayakawa et al. | 548/560 |
| 5,461,165 | 10/1995 | Domagala et al. | 548/566 |
| 5,942,629 | 8/1999 | Yuasa et al. | 548/566 |

FOREIGN PATENT DOCUMENTS

| | | |
|---|---|---|
| 778262 A2 | 6/1997 | European Pat. Off. . |
| 855390 A1 | 7/1998 | European Pat. Off. . |
| WO 94/26708 | 11/1994 | WIPO . |

OTHER PUBLICATIONS

Cocker, Wesley; Pratt, A.C.; Shannon, P.V.R.; "Preparation and the configuration of some stereoisomeric caranylamines." *Tetrahedron Letters* (1967); Issue 49; pp. 5017–5020.

Pouyet, Bernard; "Purification of aroatic amines." Univ. Lyon, Lyones, *Purif. Inorg. Org. Mater* (1969); 121–4. Editor(s): Zief, Morris; Publisher: Marcel Dekker, Inc., New York, NY; CODEN: 21BVA5.

Tavare, Narayan S.; "Industrial Crystallizaytion, Process Simulation Analysis and Design" pp. 1–5; University of Manchester Institute of Science and Technology (UMIST); Manchester, United Kingdom; published in 1995 by Plenum Press, New York, a division of Plenum Publishing Corp.; New York, NY; ISBN 0–306–44861–0.

Tipson, Stuart R.; "Crystallization and Recrystallization"; chapter II, especially pp. 396–397 of *Technique of Organic Chemistry*, vol. III, Part 1 *Separation and Purification*; Editor Weissberger, Arnold; Published in 19156 by Interscience Publishers, a division of John Wiley & Sons; London, New York, Sidney; Library of Congress catalog card No. 49–48584 (1956).

Zabicky, Jacob; "Detection, determination and characterisation of amines" Chapter 3, pp. 87–89 of *The Chemistry of the Amino Group*; Editor Patai, Saul; The Hebrew University; Jerusalem, Israel; Published in 1968 by Interscience Publishers, a division of John Wiley & Sons, London, New York, Sidney; Library of Congress catalog card No. 67–31072, SBN 470 66931 4.

International Search Report PCT/US 99/11739, dated Oct. 19, 1999.

*Primary Examiner*—Joseph K. McKane
*Assistant Examiner*—Jane C. Oswecki
*Attorney, Agent, or Firm*—Thomas A. Wootton

[57] ABSTRACT

This invention provides a novel and useful purification step in the manufacture of a diamine pyrrolidine side chain intermediate for a quinolone antibiotic that allows production of the antibiotic in significantly greater yields and at lower costs than was previously possible. Salts, procedures and processes for preparing them, including the salt disclosed in Formula A-1, below, are also disclosed.

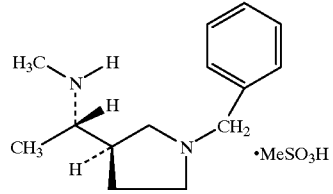

(Formula A-1)

13 Claims, No Drawings

SALTS OF DIAMINE PYRROLIDINE

CROSS-REFERENCE TO RELATED APPLICATIONS

This application claims the benefit of U.S. Provisional Application 60/087,194 filed May 29, 1998, and U.S. Provisional Application 60/101,848 filed Sep. 25, 1998, the respective disclosures of which are hereby incorporated herein by reference.

FIELD OF THE INVENTION

This invention discloses a novel salt of a pyrrolidine intermediate used in the manufacture of a quinolone antibiotic.

INFORMATION DISCLOSURE

Albright, David E., Jr., "Purification of 3,5-diaminobenzotrifluoride by selective formation of the hydrochloride salt." U.S. Pat. No. 5,130,490, issued Jul. 14, 1992, assigned to Occidental Chemical Corp., USA.

Chiou, Jackson K. S.; Jones, Ronald E., "Separation and recovery of secondary alkyl primary amines." U.S. Pat. No. 3,927,102, Issued Dec. 16, 1975, assigned to Texaco Inc., USA.

Cocker, Wesley; Pratt, A. C.; Shannon, P. V. R., "Preparation and the configuration of some stereoisomeric caranylamines." Tetrahedron Lett. (1967), Issue 49, pp. 5017–5020.

Dudzinski, Zdzislaw F., "Process of Making Aliphatic amines." U.S. Pat. No. 3,436,420 issued Apr. 1, 1969, assigned to Millmaster Onyx Corp., USA.

Domagala, et. al., "Individual Stereoisomers of Intermediate of 7-[3-(1-Aminoalkyl)-1-Pyrrolidinyl]-Quinolones and Naphthyridones as Antibacterial Agents." U.S. Pat. No. 5,461,165, issued Oct. 24, 1995, assigned to Warner-Lambert Co., USA.

Hayakawa, et. al., "3-Pyrrolidine Methanamines Wherein the Alpha-Carbon is Substituted by 1 or 2 Lower Alkyl Groups which are Intermediates for Pyridone-Carboxylic Acid Derivatives." U.S. Pat. No. 5,416,222, issued May 16, 1995, assigned to Daiichi Seiyaku Co., Japan.

Lerman, Ori; Tennenbaum, Michael; Gal, Erez; Kaspi, Joseph, "Process for the purification of (RR,SS)-2-dimethylamino)methyl-1-(3-methoxyphenyl)cyclohexanol and its salts from the (RS, SR) isomer via acid dehydration and recrystallization." Eur. Pat. Appl., EP 0778262 A2, Application: EP 96-308347.2, Published Jun. 11, 1997, assigned to Chemagis Ltd., Israel.

McWhorter, William W.; Fleck, Thomas J.; Pearlman, Bruce, A; "Optically Active 3-(1-(alkylamino)alkyl) pyrrolidines." PCT/US94/04548, See WO 94/26708, published Nov. 24, 1994, assigned to Pharmacia & Upjohn, Co., USA.

Pouyet, Bernard, "Purification of aromatic amines." Univ. Lyon, Lyons, Fr. Purif. Inorg. Org. Mater. (1969), 121–4. Editor(s): Zief, Morris. Publisher: Marcel Dekker, Inc., New York, N.Y. CODEN: 21BVA5. Conference written in English.

R. Stuart Tipson, "Crystallization and Recrystallization" Chapter II, especially pp. 396–397 of "Technique of Organic Chemistry, Vol. III, Part 1, Separation and Purification." Editor Weissberger, Arnold, Published in 1956 by Interscience Publishers, a division of John Wiley & Sons, London, New York, Sidney, Library of Congress catalog card number 49-48584.

Tavare, Narayan S., "Industrial Crystallization, Process Simulation Analysis and Design" pp. 1–5. University of Manchester Institute of Science and Technology (UMIST), Manchester, United Kingdom. Published in 1995 by Plenum Press, New York, a division of Plenum Publishing Corp., New York, N.Y., ISBN 0-306-44861-0.

Jacob Zabicky, "Detection, determination and characterisation of amines" Chapter 3, pp. 87–89 of "The Chemistry of the Amino Group." Editor Patai, Saul, The Hebrew University, Jerusalem, Israel. Published in 1968 by Interscience Publishers, a division of John Wiley & Sons, London, New York, Sidney, Library of Congress catalog card number 67-31072, SBN 470 66931 4.

BACKGROUND OF THE INVENTION

Quinolone type structures are known for their antibacterial properties, and several quinolone antibiotics (e.g. norfloxacin and ciprofloxacin) are on the market. Quinolone antibiotics may be considered as having two main structural components, the quinolone nucleus and side chains covalently bound to that nucleus. The composition of the side chain attached to the quinolone nucleus controls many of the properties of the antibiotic. Properties such as the antibiotic's potency and side effects may be strongly influenced by the structure of the side chain.

The manufacture of the side chain is a critical component in the manufacture of the quinolone antibiotic. With some quinolone antibiotics the side chain can be manufactured independently from the quinolone nucleus. This invention discloses a new method of producing a purified intermediate that can then be processed into a side chain intermediate which can be attached to a quinolone nucleus in order to produce a useful antibiotic.

Purification steps are very important in the manufacturing of pharmaceutical drugs. Every step in the manufacture of a drug requires expense in the form of operators, equipment and protocols that ensure the proper product is created. The manufacturing process and conditions must comply with both good manufacturing practices and with numerous regulations. Here we disclose a novel and useful purification step in the manufacture of a quinolone antibiotic diamine pyrrolidine side chain intermediate for a quinolone antibiotic that allows production of the antibiotic in significantly greater yields and at lower costs than was previously possible.

SUMMARY OF THE INVENTION

This invention includes a compound and a composition including a compound represented by the name (3R, 1'S)-3-[(1'-N-methylamino)ethyl-N-benzylpyrrolidine monomethanesulfonate and any of the compounds and a composition including a specific diastereomer selected from any of the diastereomers of the salts represented by the formula below,

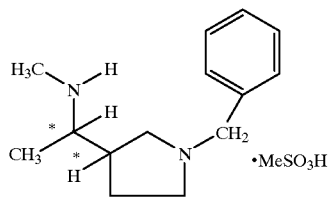

(Formula A)

where * indicates an asymmetric carbon atom.

Also included are any specific diastereomers and a composition including a specific diastereomer selected from any of possible diastereomers of the salt of the formula above, including the 4 diastereomers indicated below:

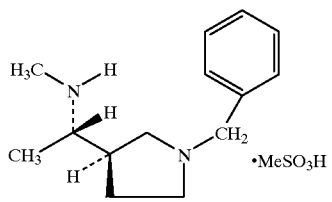

(Formula A-1)

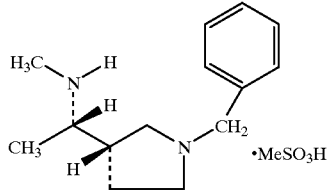

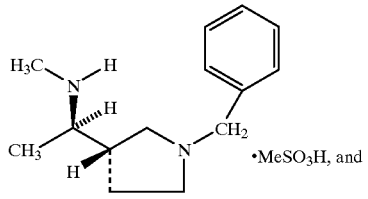

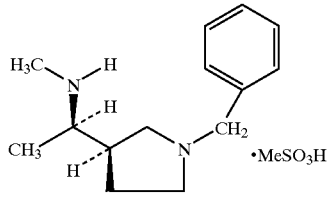

Another aspect of the invention is specific salts of formula A-1, and a composition including specific salts of formula A-1 including, a salt and a composition including a salt having the proton (1H) NMR spectra values shown below, 1H-NMR (CDCl3): 1.3 (d, 3H, J=6), 1.65 (m, 1H), 2.0 (m, 1H), 2.4–2.7 (m, 4H), 2.65 (s, 3H), 2.7 (s, 3H), 2.8 (m, 1H), 3.05 (t, 1H, J=9), 3.6 (d, 1H, J=13), 3.7 (d, 1H, J=13), 7.3 (m, 6H), 7.6 (bs, 1H);

a salt and a composition including a salt of formula A-1 having the carbon 13 (13C) NMR spectra values shown below, 13C-NMR(CDCl3): 13.69, 30.80, 39.31 (CH3); 26.33, 53.48, 56.86, 59.89 (CH2), 40.01, 58.37, 127.11, 128.26, 128.73 (CH), 138.23 (C);

a salt and a composition including a salt of formula A-1 having a melting point between about 91° C. and about 105° C.; a salt and a composition including a salt of formula A-1 having a melting point between about 91° C. and about 95° C.; and a salt and a composition including a salt of formula A-1 having a melting point between about 99° C. and about 105° C.

The invention also discloses procedures for producing a salt having the formula below:

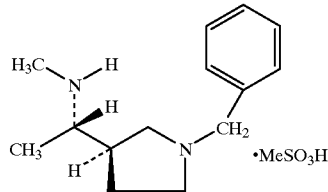

(Formula A-1)

comprising the steps of:

a) adding MeSO₃H to any stereoisomers of the diamine shown below,

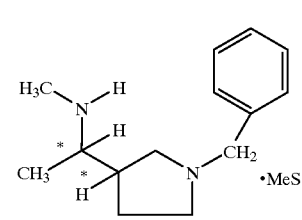

(Formula A)

where * indicates an asymmetric carbon atom.

where a * indicates an asymmetric carbon atom, b) adding sufficient solvent in which the salt is poorly soluble, and c) collecting the crystalline diamine MeSO₃H salt.

In more particular, the invention describes a process where the stereoisomers of the diamine are dissolved in an anhydrous organic solvent solution before and when the MeSO₃H is added; said solvent in which the salt is poorly soluble is also anhydrous and its volume is greater than the volume of the original anhydrous organic solvent (step a); the solution of salt and said solvent are heated and distilled until the volume reduction from distillation is 20% or more, with the distillation temperature being held to a maximum of about 80° C.; cooling said heated and distilled mixture, with the temperature being lowered to between about 60° C. to 20° C., adding previously prepared seed salt and then cooling the resulting salt solution further by cooling to between about 40 to below −20° C., filtering said solution and collecting the crystals. Crystals can be washed in cool (about 5° C. to −10° C.) THF and dried again.

More particularly, the diamine can be dissolved in CH₂Cl₂ solution before and when the MeSO₃H is added, and said solvent in which the salt is poorly soluble is THF and the volume of the THF is greater than the volume of original CH₂Cl₂ solvent, and said distillation temperature maximum is about 65° C., said heated and distilled mixture is cooled, with the temperature being lowered to about 45° C., and after said seed salt is added the resulting salt solution is further cooled to between about 20° C. to −10° C., and then filtered, and the filtrate is then washed in cool (about 0° C. to −5° C.) THF, and filtered again.

Even more particularly, the heated mixture may be cooled to about 45° C. for about 5–10 minutes, and when the seed salt is added the resulting salt solution is cooled to about 28° C. for about 5–10 minutes, then cooled to about 20° C. in about 5 min., held at 20° C. for about 1 hour, then cooled to about −10 to −5° C. in about 30 min. and filtered and then washed with 0° C. THF and dried at about 50° C.

ADDITIONAL DESCRIPTION OF THE INVENTION AND DESCRIPTION OF THE PREFERRED EMBODIMENT(S)

Definitions

CDCl$_3$ is deuterium substituted carbon tetrachloride.

Bn is benzyl or —CH$_2$-phenyl.

"Diamine" refers to either a specific compound whose formula is shown as a MeSO$_3$H salt in Formula A or it can refer to any of the diastereomers shown as benzylated precursors in Formulas C–G, or it may refer to any specific isomers of those compounds. The preferred isomer is shown in Formula A and is the (3R,1'S)-diastereomer.

Diastereomer refers to compound with a particular configuration. It is synonymous with enantiomer, stereoisomer, diastereoisomer, diastereomer and diasteriomer, all these terms may be used interchangeably in this document.

"NMR" or "nmr" is Nuclear Magnetic Resonance Spectroscopy.

"Prediamine" refers to the benzyl derivative precursor of the diamine, or it can refer to any of the diastereomers shown in Formulas C–G, or it may refer to any specific isomers of those compounds.

"THF" is tetrahydrofuran.

"XRD" is X-Ray Diffraction or Powder X-Ray Diffraction.

Units of Measure:

° C. is degree centigrade, g is gram,

Hz is Hertz,

K$_i$ is Equilibria constant for the inhibitor,

L is Liter,

M is molar or moles per liter, mg is milligram, min is minute, mHz is milliHertz, mL is milliliter, mM is milliMolar or millimoles/liter, m/z is mass per unit charge, negative numbers may be indicated with a hyphen or "−" before the number, nm is nanometers, ppm is parts per million, rpm is revolutions per minute, sec is second, slm is standard liters per minute, μL or uL is microliter, and μsec is microsecond.

Units of measure used should be obvious to one skilled in the art or they can be found in any most reference books.

DETAILS OF THE INVENTION

This invention describes a process for improving the purification yield of the reaction that starts with a crude prediamine mixture and produces purified diamine, shown in reaction Scheme I, below. Here, diamine is the quinolone antibiotic diamine pyrrolidine side chain intermediate, that would be coupled to the quinolone nucleus. The prediamine is prepared by an asymmetric process which produces a preponderance of the desired enantiomer. Here the (3R,1'S)-enantiomer, shown in Formula A-1, is preferred, but usually when produced it is not 100% isomerically pure. A process for the preparation of pyrrolidine side chain is disclosed in McWhorter et al., U.S. Pat. No. 5,773,610 (Jun. 30, 1998), the disclosure of which is incorporated by reference herein.

Formula A-1, or prediamine-MeSO$_3$H, which may be named, (3R,1'S)-3-[(1'-N-methylamino)ethyl-N-benzylpyrrolidine monomethanesulfonate, is shown below.

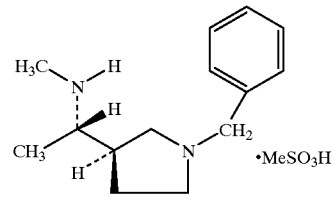

Formula A-1, or prediamine-MeSO$_3$H.

In scheme I below, the prediamine may be named (3R,1'S)-3-[(1'-N-methylamino)ethyl-N-benzylpyrrolidine. It is converted to the diamine which may be named (3R,1'S)-3-[(1'-N-methylamino)ethylpyrrolidine.

Scheme I

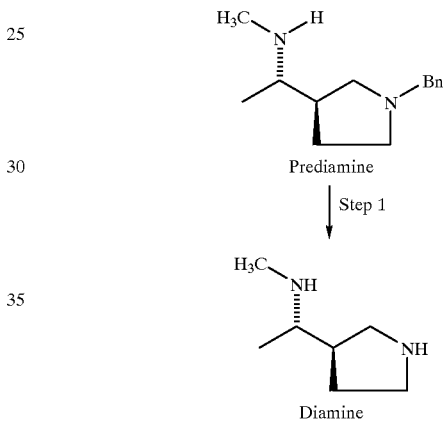

Typically, in the manufacture of diamine, the purity of prediamine has a large effect on the debenzylation and purification conditions that produce purified diamine.

Ordinarily in the typical manufacturing, process, prediamine is created in a solution that also includes byproducts or contaminates with the prediamine. Included among these byproducts are various olefinic byproducts. One such olefinic byproduct is described by Formula B, below. Such byproducts differ significantly in structure and are, therefore, relatively easy to reduce or eliminate by purification methods like distillation or pH-controlled liquid-liquid extraction.

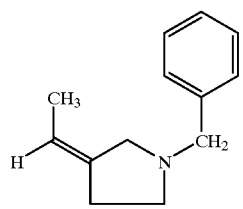

Formula B

The typical manufacturing process also creates small amounts of undesired isomeric forms of prediamine, which are much more difficult to remove. These include the (3S, 1'R)-enantiomer, the (3R,1'R)- and (3S,1'S)-diastereomers, and the 3-(2'-N-methylamino)-regioisomers shown as Formulas C–G, below. These isomeric forms are exceedingly similar in structure and reactivity to the desired (3R,1'S)-enantiomer. Unless they are removed from the process, byproducts of this type, as well as byproducts like Formula B, can significantly reduce the purity of the diamine produced and, ultimately, the purity of the final quinolone antibiotic. Therefore, purification steps are needed which efficiently produce purified diamine.

Formulas C–G (C)
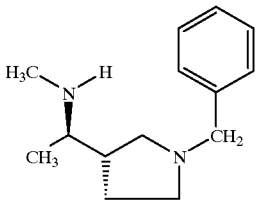

(D)
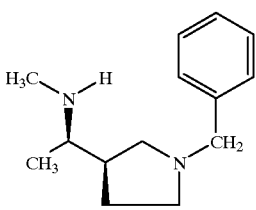

(E)
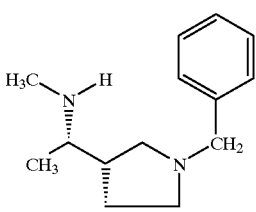

(F)
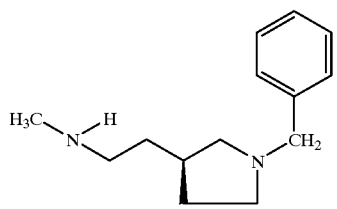

and (G)
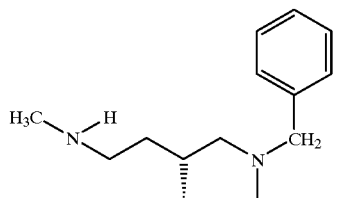

It is well known that purification by crystallization is the preferred method for removing minor contaminates which are structurally similar to the major component. Other purification methods like distillation or chromatography cannot efficiently remove isomers since they have very similar boiling points and retention characteristics. Crystallization separates such mixtures primarily on the basis of the mass of the components. A super-saturated solution of the major component is almost always not saturated in minor components of the mixture. Thus, the crystals formed are enriched in the major component and minor components are retained in solution.

The difficulty with crystallizing the diamine is that prediamine and diamine do not crystallize in their free base forms. Previous workers in this area have reported these compounds and similar analogs and they usually suggest isolation of the compounds as oils followed by purification with inefficient chromatography. See for example, Domagala, et. al., in U.S. Pat. No. 5,461,165 and Hayakawa, et. al., in U.S. Pat. No. 5,416,222. Purification by crystallization would be a big improvement but there can be no purification of the diamine by crystallization if the prediamine does not exist in crystalline form. Discovering the conditions and materials that allow the prediamine to crystallize was key to discovering a method to produce pure diamine. Purification of prediamine via crystallization was only possible after preparing an intermediate salt with a stoichiometric amount of methanesulfonic acid ($MeSO_3H$).

This purification method was the only one shown to reduce the levels of isomeric contaminates like the (3R,1'R)-diastereomer. This corresponded to an increase in the yield of purified diamine as well as purified quinolone antibiotic.

The $MeSO_3H$ salt can be created for any of the diamine isomers (see Formula A, below) and should a process be created where a different diamine isomer was favored, then the $MeSO_3H$ salt could also be prepared for that isomer, using procedures similar to those described here for the (3R,1'S)-diastereomer. Formula A, below provides a formula that shows the two asymmetric carbon atoms in the prediamine and the covalent bonds are shown as solid lines. Other formula, such as Formula A-1, show the orientation of the relevant covalent bonds, with a dotted line indicating the bond is down, into the paper and a solid wedge shaped line indicating the bond is up out of the paper. See, Formula A-1, further below.

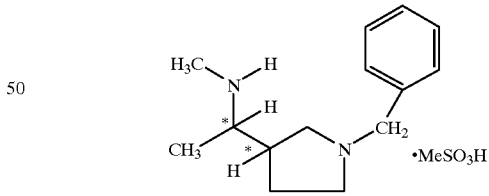

Formula A, above, where an "*" indicates an asymmetric carbon atom.

Crystal forms and purity

It is possible for the purified diamine to exist in different crystal forms. The form of the crystal can vary depending upon very slight differences in manufacture. The rate of heating or cooling, the presence of impurities, the solvents used, temperature, pressure, humidity, even gravity as well as a host of other factors can all affect crystal formation. These factors can also affect melting points of crystals. An impurity in a crystal and/or the precise form of the crystal can all affect at what temperature or range of temperatures a crystal will melt.

Here we have created several crystal forms of the desired crystals and provided data to show both proton placements (NMR data) and crystal form structure (XRD data). These examples are intended to illustrate a few of the possible crystal forms and compositions possible.

The following example shows one method of making one diasteriomer of Prediamine-MeSO$_3$H salt using prediamine which had the olefinic contaminates (like in Formula B) already removed by pH-controlled extraction. However, the process has been shown to also be effective when using typical, crude prediamine. This example is intended to illustrate and not limit the invention described above. One skilled in the art would be expected to make obvious variations and insubstantial changes from the specific conditions provided below.

Experimental for purification of prediamine via MeSO$_3$H salt

To a solution of partially purified prediamine, purified via pH 8 and pH 12 extractions (15.0 g, about 67.8 mmol, GC 98.7 area %, 1.0% (3R,1'R)-diastereomer), in CH$_2$Cl$_2$ (70 ml) at 0–2° C., slowly add MeSO$_3$H 6.67 g, 4.50 ml, 69.4 mmol, about 1.02 eq) to maintain 1–8° C. (over 7 min). Add THF (anhydrous and stabilized, 150 ml) at 0–10° C. (25 min). Distill to 90 ml total volume atmospherically (135 min, max pot temp 65° C.). Cool to 45° C. (10 min) and seed with previously made salt. Crystals form 2 min later at 40° C. Cool to 28° C. (8 min) before applying cold H$_2$O bath. Cool to 20° C. (5 min) and hold 1 hr. Cool with ice-salt bath to −10 to 0° C. (30 min, −8° C.) and filter. Wash with cold THF (0° C., 2×22 ml). Dry overnight in vacuum oven at 50° C. to give crystals (18.95 g, GC 99% with 0.5% (3R,1'R)-diastereomer, about 89% of theory).

Dissolve a portion of the salt (18.0 g) in CH$_2$Cl$_2$ (90 ml) and stir with H$_2$O (90 ml) while adding 50% aqueous NaOH dropwise to pH 11.8–12 (2.3 ml from pH 7.8 to 11.9). Allow phases to separate, remove the lower CH$_2$Cl$_2$ phase, and extract the aqueous phase with CH$_2$Cl$_2$ (90 ml, pH still 12). Combine the two CH$_2$Cl$_2$ phases and remove solvent by rotovap and high-vacuum pump to give an oil (12.3 g, about 98% recovery). This sample was dissolved in MeOH and hydrogenated to diamine (6.89 g, GC 98% area with 0.5% (3R,1'R)-diastereomer, 99% chemical yield).

The resulting salt has the formula of Formula A-1, or prediamine-MeSO$_3$H, shown below.

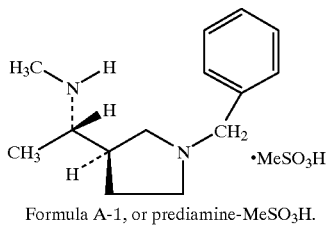

Formula A-1, or prediamine-MeSO$_3$H.

(3R,1'S)-3-[(1'-N-methylamino)ethyl-N-benzylpyrrolidine monomethanesulfonate

The formation of a prediamine- MeSO$_3$H salt can provide an easy method of producing large amounts of relatively pure diamine.

Confirmation of the structure of Formula A-1 by NMR spectroscopy Nuclear Magnetic Resonance (NMR) spectroscopy was used to confirm the structure of Formula A. Both proton and 13C NMRs were performed. The equipment parameters and spectra and interpretation are provided here.

NMR data were recorded on a Bruker AMX300 operating at 300.13 MHz for the observation of 1H and 75.40 MHz for the observation of 13C. Samples were dissolved in, and internally referenced to, CDCl3 (1H, d=7.26; 13C, d=77.0). One dimensional NMR data were recorded as a 32k complex point data table with a 10,600 Hz sweep width for proton and 20,800 Hz sweep width for carbon. The number of transients and various pulse widths are listed in the appropriate figures. 1H experiments were processed with gaussian multiplication and 13C with a 2 Hz exponential multiplication prior to fourier transformation. The spectral data and interpretation provided follow standard abbreviations—d is doublet, m is multiplet, s is singlet, t is triplet, H is hydrogen, J is coupling constant in hertz. The values provided are chemical shifts in ppm (parts per million) from the reference peak.

Proton NMR.

Data Parameters: EXPNO is 11, PROCNO is 1.

Acquisition Parameters: SOLVENT is CDCl13, AQ is 1.3271240 sec, FIDRES is 0.376760 Hz, DW is 81.0 μsec., RG is 4096, NUCLEUS is 1H, HL1 is 1 dB, D1 is 3.0 sec., P1 is 10.3 μsec., DE is 101.3 μsec., SFO1 is 300.1351620 MHz, SWH is 6172.84 Hz, TD is 16384, NS is 16, DS is 2.

Processing parameters: SI is 16384, SF is 300.1333581 MHz, WDW is GM, SSB is 0, LB is −0.30 Hz, GB is 0.15, PC is 3.00.

Proton NMR spectra and interpretation:
1H-NMR (CDCl3): 1.3 (d, 3H, J=6), 1.65 (m, 1H), 2.0 (m, 1H), 2.4–2.7 (m, 4H), 2.65 (s, 3H), 2.7 (s, 3H), 2.8 (m, 1H), 3.05 (t, 1H, J=9), 3.6 (d, 1H, J=13), 3.7 (d, 1H, J=13), 7.3 (m, 6H), 7.6 (bs, 1H);

13C NMR.

Data Parameters: EXPNO is 14, PROCNO is 1.

Acquisition Parameters: SOLVENT is CDCl3, AQ is 0.327700 sec, FIDRES is 1.525879 Hz, DW is 20.0 μsec., RG is 4096, NUCLEUS is 13C, HL1 is 1 dB, D1 is 1.0 sec., S1 is 1 dB, P3 is 9.0 μsec., SFO2 is 300.1346670 MHz, D2 is 0.0035714 sec., P4 is 18.0 μsec., P1 is 7.0 μsec., P2 is 14.0 μsec., S2 is 22 dB, DE is 25.0 μsec., SFO1 is 75.4753020 MHz, SWH is 25000.00 Hz, TD is 16384, P31 is 100.0 μsec., NS is 256, DS is 4.

Processing parameters: SI is 16384, SF is 75.4685977 MHz, WDW is EM, SSB is 0, LB is 2.00 Hz, GB is 0, PC is 1.40.

13C-NMR spectra and interpretation:
13C-NMR (CDCl3): 13.69, 30.80, 39.31 (CH3); 26.33, 53.48, 56.86, 59.89 (CH2), 40.01, 58.37, 127.11, 128.26, 128.73 (CH), 138.23 (C)

Confirmation of the structure of Formula A-1 by XRD spectroscopy

A Rigaku DMAX-A X-ray diffractometer is employed for the acquisition of the powder XRD patterns. The instrument is operated with the copper K-L$_3$ radiation at 1.5406 Å. The major instrumental parameters are set as follows: 40 KV voltage, 30 mA current, beam aperture of 1° and detector aperture (receiving slit) of 0.30°. Patterns are scanned over the range of 3–40° two-theta angles with a scan rate of 1.5° two-theta/min (step size of 0.05° and counting time at 2 second/step). Samples are ground to fine powders and packed into an aluminum tray. Complete description of the parameters and abbreviations used below may be found in either the operations manual for the Rigaku DMAX-A X-ray diffractometer, or they may be found in most XRD manuals.

Peak Reports for three different crystals are provided here. The first report, below, shows the spectra for a crystal with a melting point between about 99 and 105° C.

| | | Number 1. Area Sum: 8308.309 | | | | |
|---|---|---|---|---|---|---|
| STD | Center X | Height | Width | Area | Qty | Name |
| 0 | 5.834918 | 1092.0131 | .8751047 | 224.19034 | 0 | 5.83 |
| 0 | 9.9110054 | 383.73329 | .8273052 | 104.87254 | 0 | 9.91 |
| 0 | 11.13072 | 451.63211 | .585815 | 94.732384 | 0 | 11.13 |
| 0 | 11.69375 | 528.70474 | .666675 | 114.14881 | 0 | 11.69 |
| 0 | 14.795333 | 1797.9825 | 1.455302 | 479.67671 | 0 | 14.79 |
| 0 | 15.921212 | 1476.2741 | .951913 | 363.07695 | 0 | 15.92 |
| 0 | 17.471698 | 1855.8032 | 1.323417 | 677.98383 | 0 | 17.47 |
| 0 | 18.475686 | 410.45285 | .503866 | 75.167063 | 0 | 18.47 |
| 0 | 19.023329 | 3268.1195 | 1.237003 | 971.86381 | 0 | 19.02 |
| 0 | 19.219853 | 873.31139 | .261395 | 152.85561 | 0 | 19.22 |
| 0 | 19.605024 | 2792.0912 | .424057 | 540.56151 | 0 | 19.6 |
| 0 | 19.975194 | 357.01175 | .541624 | −51.32979 | 0 | 19.97 |
| 0 | 21.241494 | 2645.4923 | 1.175444 | 1083.6633 | 0 | 21.24 |
| 0 | 22.891667 | 1559.2777 | 1.301086 | 606.35257 | 0 | 22.89 |
| 0 | 23.521112 | 913.09385 | .494843 | 222.95287 | 0 | 23.52 |
| 0 | 24.133978 | 1019.5988 | .554393 | 345.74773 | 0 | 24.13 |
| 0 | 24.508086 | 1264.6217 | .392158 | 336.29395 | 0 | 24.51 |
| 0 | 25.017281 | 1913.1805 | 1.519106 | 632.57096 | 0 | 25.02 |
| 0 | 25.401105 | 215.86944 | .817443 | 248.49867 | 0 | 25.4 |
| 0 | 25.918957 | −87.41223 | 1.569454 | −370.6186 | 0 | 25.92 |
| 0 | 26.815625 | 132.78142 | .462531 | 31.495602 | 0 | 26.81 |
| 0 | 27.092949 | 123.79176 | .690996 | 42.244557 | 0 | 27.09 |
| 0 | 28.224462 | 600.42504 | .859375 | 193.27808 | 0 | 28.22 |
| 0 | 28.830992 | 610.87875 | .608551 | 167.68869 | 0 | 28.83 |
| 0 | 29.488636 | 324.3707 | .623618 | 97.977263 | 0 | 29.49 |
| 0 | 30.005232 | 222.75713 | .582108 | 70.931509 | 0 | 30 |
| 0 | 31.122761 | 255.15629 | .854026 | 79.714945 | 0 | 31.12 |
| 0 | 32.5 | 92.051473 | .582163 | 29.329946 | 0 | 32.5 |
| 0 | 33.162097 | 266.93974 | .52954 | 61.269216 | 0 | 33.16 |
| 0 | 33.745714 | 71.357752 | .569382 | 20.886694 | 0 | 33.74 |
| 0 | 34.668382 | 146.45223 | .992 | 65.5167 | 0 | 34.67 |
| 0 | 35.547222 | 255.87001 | .609394 | 68.453135 | 0 | 35.55 |
| 0 | 35.984862 | 156.83937 | .577744 | 36.357722 | 0 | 35.98 |
| 0 | 37.268038 | 242.6646 | .917453 | 94.268565 | 0 | 37.27 |
| 0 | 37.880357 | 75.850116 | .463806 | 16.364475 | 0 | 37.88 |
| 0 | 38.438983 | 1012.3131 | 1.606297 | 350.42475 | 0 | 38.44 |
| 0 | 39.473034 | 119.39596 | .555893 | 28.845653 | 0 | 39.47 |

The second report, below, shows the spectra for a crystal with a melting point between about 99 and 105° C.

| | | Number 2. Area Sum: 13396.29 | | | | |
|---|---|---|---|---|---|---|
| STD | Center X | Height | Width | Area | Qty | Name |
| 0 | 5.9715556 | 7027.6799 | 1.3933285 | 1240.5507 | 0 | 5.97 |
| 0 | 9.8595943 | 802.23455 | .95033977 | 157.99408 | 0 | 9.86 |
| 0 | 11.128762 | 962.72309 | .83826671 | 185.32174 | 0 | 11.13 |
| 0 | 11.933489 | 5107.8936 | 1.1434835 | 843.2251 | 0 | 11.93 |
| 0 | 12.979861 | 248.5398 | .59978733 | 41.478462 | 0 | 12.98 |
| 0 | 14.770327 | 797.52601 | .99394451 | 164.05737 | 0 | 14.77 |
| 0 | 15.223529 | 158.05241 | .49794698 | 29.780324 | 0 | 15.22 |
| 0 | 16.608459 | 1287.2919 | 1.0963857 | 267.2659 | 0 | 16.61 |
| 0 | 17.657398 | 4447.2803 | .72198886 | 1065.9162 | 0 | 17.66 |
| 0 | 17.927192 | 4573.0339 | .54387841 | 819.07926 | 0 | 17.93 |
| 0 | 18.884714 | 4399.7459 | .62235323 | 916.47831 | 0 | 18.88 |
| 0 | 19.085128 | 6096.8224 | .50971719 | 1123.0525 | 0 | 19.08 |
| 0 | 19.810571 | 470.83092 | .4129033 | 60.143712 | 0 | 19.81 |
| 0 | 20.200498 | 4813.3296 | .95528902 | 1137.7599 | 0 | 20.2 |

-continued

Number 2. Area Sum: 13396.29

| STD | Center X | Height | Width | Area | Qty | Name |
|---|---|---|---|---|---|---|
| 0 | 20.964015 | 186.93076 | .40539918 | 28.206431 | 0 | 20.96 |
| 0 | 21.827907 | 1762.838 | .77977651 | 420.34597 | 0 | 21.83 |
| 0 | 22.271059 | 1275.6447 | .58514569 | 314.27325 | 0 | 22.27 |
| 0 | 22.990567 | 1508.8252 | .73054087 | 315.12441 | 0 | 22.99 |
| 0 | 24.015809 | 5758.6184 | 1.3634189 | 1336.4861 | 0 | 24.01 |
| 0 | 24.444188 | 599.2165 | .84461837 | 425.62015 | 0 | 24.44 |
| 0 | 25.029239 | 927.12006 | .66213916 | 207.90402 | 0 | 25.03 |
| 0 | 25.818684 | 1492.6358 | .89375199 | 428.21817 | 0 | 25.82 |
| 0 | 26.035822 | 177.30743 | .28641852 | 26.096782 | 0 | 26.03 |
| 0 | 26.413524 | 4.2728519 | .38634407 | 1.1535085 | 0 | 26.41 |
| 0 | 27.394792 | 926.09227 | .76494323 | 209.49965 | 0 | 27.39 |
| 0 | 28.655916 | 1440.6638 | .87687014 | 406.14477 | 0 | 28.65 |
| 0 | 30.127184 | 703.33693 | 1.1222087 | 231.53941 | 0 | 30.13 |
| 0 | 30.818846 | 142.60067 | .52772255 | 25.706841 | 0 | 30.82 |
| 0 | 31.613529 | 783.3234 | .80394348 | 186.49975 | 0 | 31.61 |
| 0 | 32.213596 | 374.77607 | .80186508 | 108.73435 | 0 | 32.21 |
| 0 | 33.170833 | 391 | .94545542 | 125.11446 | 0 | 33.17 |
| 0 | 35.032308 | 76.362971 | .40026442 | 15.120593 | 0 | 35.03 |
| 0 | 35.577371 | 451.05412 | 1.2308229 | 187.78989 | 0 | 35.58 |
| 0 | 36.349167 | 360.65748 | .6245618 | 75.278669 | 0 | 36.35 |
| 0 | 38.433815 | 895.70864 | .89174144 | 216.18376 | 0 | 38.43 |
| 0 | 39.676202 | 179.07396 | .65 | 53.15 | 0 | 39.68 |

The third report, below, shows the spectra for a crystal with a melting point between about 91 and 95° C.

Number 3. Area Sum: 9154.595

| STD | Center X | Height | Width | Area | Qty | Name |
|---|---|---|---|---|---|---|
| 0 | 5.9153846 | 944.01017 | 1.0937917 | 271.89777 | 0 | 5.91 |
| 0 | 9.8864754 | 424.13142 | .73957126 | 82.445475 | 0 | 9.89 |
| 0 | 11.137689 | 458.44108 | .72857206 | 90.561068 | 0 | 11.14 |
| 0 | 11.736436 | 295.01043 | .42062792 | 57.883083 | 0 | 11.74 |
| 0 | 11.912097 | 270.45386 | .35773856 | 45.651294 | 0 | 11.91 |
| 0 | 14.799397 | 1473.0095 | 1.0211427 | 288.99874 | 0 | 14.8 |
| 0 | 15.929309 | 908.03285 | .76254095 | 197.24495 | 0 | 15.93 |
| 0 | 16.631835 | 775.74021 | .71458333 | 184.31585 | 0 | 16.63 |
| 0 | 17.518764 | 1458.3208 | .69189122 | 377.16544 | 0 | 17.52 |
| 0 | 17.681298 | 1401.3277 | .17642639 | 223.97892 | 0 | 17.68 |
| 0 | 17.928364 | 1766.818 | .42884906 | 384.66641 | 0 | 17.93 |
| 0 | 18.493333 | 198.697 | .40320057 | 32.965388 | 0 | 18.49 |
| 0 | 19.06505 | 3318.8726 | 1.1921022 | 1589.6955 | 0 | 19.06 |
| 0 | 19.617385 | 2315.4976 | .48113491 | 671.13181 | 0 | 19.62 |
| 0 | 20.19373 | 2687.976 | .8195737 | 842.38561 | 0 | 20.19 |
| 0 | 20.571512 | 164.77539 | .25451639 | 23.855266 | 0 | 20.57 |
| 0 | 21.266521 | 1431.421 | .82361901 | 613.48087 | 0 | 21.27 |
| 0 | 21.845448 | 1036.8835 | .52982799 | 258.09355 | 0 | 21.84 |
| 0 | 22.2898 | 786.16844 | .46039375 | 203.43032 | 0 | 22.29 |
| 0 | 22.922488 | 979.30254 | .74892663 | 360.64567 | 0 | 22.92 |
| 0 | 23.529706 | 438.59226 | .41670751 | 110.79993 | 0 | 23.53 |
| 0 | 24.121519 | 948.97611 | .60244684 | 379.03961 | 0 | 24.12 |
| 0 | 24.48561 | 1424.7514 | .43338209 | 349.13472 | 0 | 24.48 |
| 0 | 25.039211 | 1521.3687 | .86442201 | 432.59769 | 0 | 25.04 |
| 0 | 25.418595 | 201.42547 | .28827287 | 28.952083 | 0 | 25.42 |
| 0 | 27.412277 | 463 | .69236495 | 122.18741 | 0 | 27.41 |
| 0 | 28.263393 | 320.80197 | .491224 | 89.646156 | 0 | 28.26 |
| 0 | 28.690079 | 403.3547 | .72602709 | 151.88305 | 0 | 28.69 |
| 0 | 29.518939 | 176.73902 | .50940204 | 50.783171 | 0 | 29.52 |
| 0 | 29.990476 | 199.61121 | .68674462 | 83.839193 | 0 | 29.99 |
| 0 | 31.163587 | 92.31139 | .50992405 | 19.136831 | 0 | 31.16 |
| 0 | 32.219697 | 107.07185 | .61296813 | 26.201445 | 0 | 32.22 |
| 0 | 33.177174 | 302.24777 | 1.2885351 | 86.682518 | 0 | 33.18 |
| 0 | 33.7375 | 59.417303 | .56476314 | 20.061035 | 0 | 33.74 |
| 0 | 35.530078 | 231.34934 | .705873 | 58.259443 | 0 | 35.53 |
| 0 | 37.27931 | 108.05567 | .78690464 | 30.966579 | 0 | 37.28 |
| 0 | 38.444396 | 1006.0711 | 1.0134273 | 280.65145 | 0 | 38.44 |
| 0 | 39.670588 | 88.837647 | .9375 | 33.279688 | 0 | 39.67 |

What is claimed is:

1. A composition comprising the compound represented by the name (3R,1'S)-3-[(1'-N-methylamino)ethyl]-N-benzylpyrrolidine monomethanesulfonate.

2. A composition comprising a stereoisomer salt selected from the group consisting of:

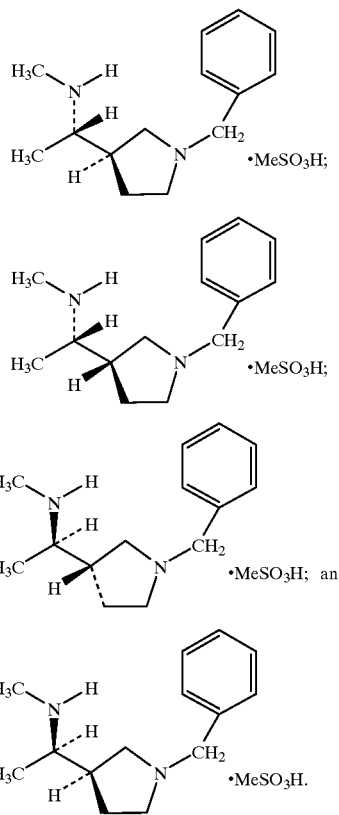

(Formula A-1)

3. A composition according to claim 2 wherein the stereoisomer salt has the formula

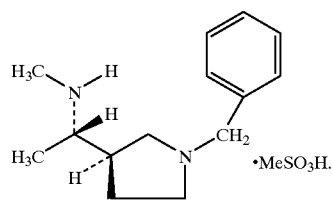

(Formula A-1)

4. A composition comprising the salt of claim 3, said salt having the proton (1H) NMR spectra values shown below:

1H-NMR (CDCl3): 1.3 (d, 3H, J=6), 1.65 (m, 1H), 2.0 (m, 1H), 2.4–2.7 (m, 4H), 2.65 (s, 3H), 2.7 (s, 31), 2.8 (m, 1H), 3.05 (t, 1H, J=9), 3.6 (d, 1H, J=13), 3.7 (d, 1H, J=13), 7.3 (m, 6H), 7.6 (bs, 1H).

5. A composition comprising the salt of claim 3, said salt having the carbon 13(13C) NMR spectra values shown below:

13C-NMR (CDCl3): 13.69, 30.80, 39.31 (CH3); 26.33, 53.48, 56.86, 59.89 (CH2), 40.01, 58.37, 127.11, 128.26, 128.73 (CH), 138.23 (C).

6. A composition comprising the salt of claim 3, said salt having a melting point between about 91° C. and about 105° C.

7. A composition comprising the salt of claim 5, said salt having a melting point between about 91° C. and about 95° C.

8. A composition comprising the salt of claim 5, said salt having a melting point between about 99° C. and about 105° C.

9. A process for producing the salt having the formula

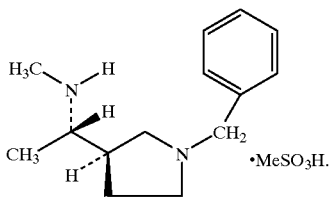

(Formula A-1)

comprising the steps of
a) adding MeSO₃H to any stereoisomers of the diamine shown below,

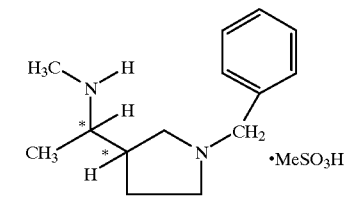

where a * indicates an asymmetric carbon atom;
b) adding sufficient solvent in which the salt is poorly soluble;
c) collecting the crystalline diamine MeSO₃H salt.

10. The process of claim 9 comprising the steps of:
a) in step a of claim 9, dissolving the stereoisomers of the diamine in an anhydrous organic solvent solution before and when the MeSO₃H is added;
b) in step b of claim 9, said solvent in which the salt is poorly soluble is anhydrous and its volume is greater than the volume of the original anhydrous organic solvent, step a of the present claim;
c) after step b of claim 9, heating and distilling the solution of salt and said solvent until the volume reduction from distillation is 20% or more, and holding the distillation temperature to a maximum of about 80° C.;
d) after step c of the present claim, cooling said heated and distilled mixture, and lowering the temperature to between about 60° C. to 20° C.; and
e) after step d of the present claim, adding previously prepared seed salt and then cooling the resulting salt solution further by cooling to between about 40 to below −20° C., filtering said solution, and collecting the crystals.

11. The process of claim 10, comprising the steps, after step (e) of claim 10, of washing the crystals in cool, about 5° C. to −10° C., THF after the crystals are filtered and drying the washed crystals.

12. The process of claim 11 wherein:
said solvent in which the diamine is dissolved before and when the MeSO₃H is added is CH₂Cl₂;

said solvent in which the salt is poorly soluble is THF and the volume of the THF is greater than the volume of original $CH_2Cl_2$ solvent; and said distillation temperature maximum is about 65° C., said process comprising the steps of:

cooling said heated and distilled mixture to a temperature of about 45° C.;

after said seed salt is added, further cooling the resulting salt solution to between about 20° C. to −10° C., and then filtering the solution; and after the crystals are filtered, washing the crystals in cool, about 0° C. to −5° C., THF, and then filtering the crystals again.

13. The process of claim 12 comprising the steps of:

cooling said heated mixture to about 45° C. for about 5 to 10 minutes;

adding said seed salt and cooling the resulting salt solution to about 28° C. for about 5 to 10 minutes, then cooling the solution to about 20° C. in about 5 min, holding the solution at 20° C. for about 1 hour, then cooling the solution to about −10 to −5° C. in about 30 min.; and filtering and then washing the crystals with 0° C. THF and drying the crystals at about 50° C.

\* \* \* \* \*